United States Patent [19]

Bahar et al.

[11] Patent Number: 5,242,804
[45] Date of Patent: Sep. 7, 1993

[54] SIMULTANEOUS DUAL ANALYTE ASSAY

[75] Inventors: Izak Bahar, Chestnut Hill; Francis X. Cole, Stow; L. Edward Cannon, Wayland, all of Mass.

[73] Assignee: Hygeia Sciences, Inc., Newton, Mass.

[21] Appl. No.: 834,990

[22] Filed: Feb. 14, 1992

Related U.S. Application Data

[63] Continuation of Ser. No. 326,337, Mar. 21, 1989, abandoned.

[51] Int. Cl.$^5$ .................... G01N 33/53; G01N 33/543
[52] U.S. Cl. .................... 435/7.93; 435/7.1; 435/7.9; 435/810; 435/972; 436/501; 436/518; 436/523; 436/536; 436/538; 436/540; 436/819
[58] Field of Search ............... 435/7.1, 810, 972, 7.93, 435/7.9; 436/501, 518, 523, 536, 538, 540, 819

[56] References Cited

U.S. PATENT DOCUMENTS

| | | | |
|---|---|---|---|
| 4,313,734 | 2/1982 | Leuvering | 436/525 |
| 4,952,517 | 8/1990 | Bahar | 436/518 |

FOREIGN PATENT DOCUMENTS 0238353 9/1987 European Pat. Off. .

OTHER PUBLICATIONS

Nakane, P. K., et al., *J. Histochem. & Cytochem.*, vol. 22, No. 12, pp. 1084–1091 (1974).
*Dictionary of Immunology*, Third Edition, W. J. Herbert, ed. Blackwell Scientific Publications, Oxford, UK, pp. 165 & 17, 1987.
*Dictionary of Immunology*, ed. W. J. Herbert, Blackwell Scientific Publications, Osney Mead, Oxford, UK, p. 187 (1985).

*Primary Examiner*—Esther L. Kepplinger
*Assistant Examiner*—Toni R. Scheiner
*Attorney, Agent, or Firm*—Staas & Halsey

[57] ABSTRACT

A simultaneous dual analyte assay for determining the fertile period of the human menstrual cycle. The assay utilizes a capture reaction component consisting of P-3-G immobilized on a microporous membrane, a blocking reaction component consisting of anti $E_1$-3-G antibody, a labelled reaction component consisting of gold particle labelled anti $E_1$-3-G antibody, and an ambifunctional reaction component consisting of a hybrid immunoreactive substance having an anti P-3-G antibody binding site and a plurality of $E_1$-3-G determinant binding sites. An aqueous sample containing P-3-G and $E_1$-3-G is contacted with the components and the assay is calibrated to provide a positive assay result only when the concentration of P-3-G in the sample is less than a predetermined concentration and the concentration of $E_1$-3-G in the sample is more than a preselected concentration whereby a visually inspectable quantity of an immunocomposite is produced that consists of both the P-3-G immobilized on the microporous membrane and the gold labelled anti $E_1$-3-G antibody.

42 Claims, 2 Drawing Sheets

5,242,804

SIMULTANEOUS DUAL ANALYTE ASSAY

This application is a continuation of application Ser. No. 07/326,337, filed Mar. 21, 1989, now abandoned.

BACKGROUND OF THE INVENTION

1. Field of the Invention

The present invention relates to an immunoassay for determining the relative concentrations of two different immunogenic analytes. In particular, the invention relates to an assay for determining relative concentrations, in a single sample, of related hormonal metabolites such as pregnanediol-3-glucuronide (P-3-G) and estrone-3-glucuronide ($E_1$-3-G). Even more particularly, the invention relates to an immunoassay suitable for testing for constituents in human urine to determine the human fertile period, that is, the period in which viable sperm and a viable ovum may be present simultaneously in the female reproductive tract.

2. The Prior Art Background

For a number of reasons it may be clinically and/or diagnostically desirable to determine the relative concentrations of two separate immunogenically reactive analytes in a single sample. In some instances, mammalian hormonal activity and/or metabolism creates situations where the relationships between concentrations of hormones or metabolites in body fluids are chronologically related to other events. In particular, the relative concentrations of P-3-G and $E_1$-3-G in human urine may be used to ascertain the fertile period of the menstrual cycle. And since, for a variety of reasons, contraceptive devices and materials may not be available for use, techniques such as immunoassays for determining the fertile period of the menstrual cycle have become desirable.

The human menstrual cycle is governed by the cyclical release of hormones from the female glands and organs. Such release is predictable and specifically related to ovulation by which ova are released from the ovaries and the lining of the uterus is made ready for pregnancy. Eventually, the released hormones and/or metabolites thereof find their way into the urine. The specific biological phenomena are described in detail and with clarity in European Patent Publication No. 0086095, published Aug. 17, 1983 in European Patent Office Bulletin 83/33. And suffice it to say, that during a normal menstrual cycle, the level of $E_1$-3-G in female urine begins to rise about 6 days prior to ovulation, reaches its peak about 1 day before ovulation and falls rapidly during and after ovulation. The level of P-3-G in female urine begins to rise on the day of ovulation, reaches its peak 2 to 3 days after ovulation and remains elevated for the duration of the luteal phase. The relationships between P-3-G and $E_1$-3-G levels are known, and from the '095 European patent publication identified above, the ratio of estrogen metabolites to progestin metabolites in the urine has been found to be useful in monitoring the progress of the menstrual cycle.

Of particular importance in following the menstrual cycle by determining hormonal activity is the fact that during the most fertile period, the level of $E_1$-3-G in the urine is approximately 20 times the level of P-3-G or greater. Thus, a simple and reliable assay capable of determining and/or detecting that period of time when the $E_1$-3-G/P-3-G ratio is 20 or greater would be extremely valuable in determining whether the female is fertile.

In the '095 patent publication identified above, an immunoassay procedure is disclosed for determining the relative concentrations of antigens in a single sample. The immunoassay employs a dual ligand molecule comprising two different antigens irreversibly bound together through a bridge support molecule to present an elongated ligand molecule having an antigenic moiety at one end and a different antigenic moiety at the other end. Bridge length is said to be crucial to the avoidance of steric hinderance and it has been found that the assay itself is sensitive to the dual ligand concentration.

The assay described in the '095 patent publication was said to be an improvement over the assay described in British Patent Specification No. GB 2029011B which includes a synthetic bifunctional ligand prepared by coupling two different antigenic moieties through a protein linkage such as bovine serum albumin (BSA). However, the number of molecules of each steroid per molecule of BSA may be independently varied by adjusting the stoichiometry of the reagents and calibration remains difficult. And as outlined in the '095 disclosure, the procedure of the '011B patent specification does not always provide for sensitive assay results because of the tendency of the bifunctional ligand to form multivalent immunocomplexes and to react nonspecifically.

SUMMARY OF THE INVENTION

The dual analyte immunoassay procedure of the present invention addresses the difficulties inherent in the prior art procedures and provides a novel assay procedure which employs an ambifunctional hybrid conjugate containing at least one antigen binding site of an anti P-3-G antibody molecule or P-3-G hormone receptor and a plurality of antigenic determinant regions of an $E_1$-3-G molecule. Through the use of such conjugate and the procedural aspects of the present invention, an immunoassay is provided for determining the relative concentrations of first and second immunoreactive analytes in a single aqueous sample. In accordance with an important aspect of the invention, the first and second immunoreactive analytes may be antigenic metabolites of hormones, namely P-3-G and $E_1$-3-G. In particular, the present invention provides a procedure for determining the human fertile period by detecting, in human urine, those instances when the ratio of $E_1$-3-G to P-3-G is above a preselected threshold level.

In its broadest aspects the present invention provides methodology and kits of materials useful in connection with dual analyte immunoassays generally. In particular, the invention provides an assay procedure for determining the relative concentrations of first and second immunoreactive analytes in an aqueous sample. The analytes need not be, but generally are, metabolically related, and the present invention is directed to determining the relative concentrations thereof and providing a signal whenever the ratio of one analyte to the other exceeds a preselected level. By appropriate empirical manipulation and calibration, the assay procedure may be designed to provide a positive result at any preselected ratio of analytes, one to the other.

In accordance with the invention, an assay procedure is provided for determining the relative concentrations of first and second immunoreactive analytes in an aqueous sample. The assay procedure includes the steps of providing a capture reaction component comprising a first immunoreactive substance having an immunospecific reactivity that is analogous to the immunospecific reactivity of the first immunoreactive analyte. The first immunoreactive substance is initially coupled to a solid support or is adapted to be coupled to a solid support. The assay procedure further includes the step of providing a blocking reaction component comprising a second immunoreactive substance that is capable of binding immunospecifically with the second immunoreactive analyte. Also provided, in accordance with the broadest aspects of the invention, is a labelled reaction component comprising a third immunoreactive substance and a detectable tag coupled thereto. The third immunoreactive substance has an immunospecific reactivity that is analogous to the immunospecific reactivity of the second immunoreactive substance.

As an important element, the invention also involves the provision of an ambifunctional linking reaction component comprising a hybrid immunoreactive substance having at least a first immunoreactive site that is capable of binding immunospecifically with either the first immunoreactive analyte or the first immunoreactive substance. The hybrid immunoreactive substance also has at least a second immunoreactive site that has an immunospecific reactivity that is analogous to the immunospecific reactivity of the second immunoreactive analyte. Thus, the second site of the hybrid immunoreactive substance is capable of binding immunospecifically with either of the second and third immunoreactive substances.

In accordance with the invention, the procedure involves the step of contacting the aqueous sample with (1) the capture reaction component, (2) an amount of the ambifunctional linking component that is sufficiently low relative to the capture reaction component that binding between the first immunoreactive site of the hybrid substance and the first immunoreactive substance of the capture component is inhibited by the presence of at least a predetermined concentration of the first analyte in the sample to such a degree that the amount of ambifunctional component able to bind to the first immunoreactive substance is too low to support a positive assay result, (3) the labelled reaction component, and (4) an amount of the blocking component that is sufficiently large to block the second immunoreactive sites of the hybrid substance and inhibit binding between the latter and the second immunoreactive substance of the labelled component in the absence of at least a preselected concentration of the second analyte in the sample to such a degree that the amount of labelled component able to bind to the second site of the hybrid substance is too low to support a positive assay result. Thus, a positive assay result is achievable only when the concentration of first analyte in the sample is less than the predetermined concentration thereof and the concentration of the second analyte in the sample is more than the preselected concentration thereof, whereby to produce a determinable quantity of an immunocomposite that comprises both the capture component and the labelled reaction component.

In a more specific aspect of the invention, at least one of the immunoreactive analytes may be antigenic, and in a preferred aspect of the invention, both are antigenic. More specifically, the analytes may be steroidal, preferably may be hormonal in nature and even more preferably may be naturally occurring mammalian steroid hormones or metabolites thereof. In a particularly preferred aspect of the invention, the first immunoreactive analyte is P-3-G and the second immunoreactive analyte is $E_1$-3-G.

In another important aspect of the invention, the solid support may comprise a microporous membrane. In another important aspect of the invention, the solid support may comprise a dispersible, water insoluble particle and the first immunoreactive substance is coupled to the particle prior to the contacting step.

In yet another important aspect of the invention, the detectable tag may be a gold sol particle.

The hybrid, ambifunctional immunoreactive substance may include a first proteinaceous substance comprising a first immunoreactive site and a second proteinaceous substance comprising a second immunoreactive site, with the first and second proteinaceous substances being irreversibly bound together to present the hybrid substance.

In accordance with the procedural aspects of the invention, during the contacting step the sample may be contacted with the blocking component before it is contacted with the labelled component.

In another procedural aspect, the blocking component, the ambifunctional linking component, and the solid phase component may all be brought into contact with the aqueous sample to produce a solid test intermediate phase, and the test intermediate phase may then be contacted with the labelled component to produce a test result phase.

The first immunoreactive substance may be coupled to the solid support prior to the contacting step. Alternatively, the first immunoreactive substance may be coupled to the solid support after the contacting step.

Preferably, the assay procedure of the present invention may be used for predicting the fertile period of the menstrual cycle, and in this event the first analyte may be P-3-G, the second analyte may be $E_1$-3-G, the first immunoreactive substance may be P-3-G, the second and third immunoreactive substances may be the same antibody to $E_1$-3-G, the first immunoreactive site of the ambifunctional substance may be provided by an antigen binding site of an antibody to P-3-G and the second immunoreactive site of the ambifunctional substance may be provided by an antigenic determinant region of an $E_1$-3-G molecule. In this preferred aspect of the invention, the antibody to P-3-G and the $E_1$-3-G molecule are irreversibly bound together to present the ambifunctional hybrid immunoreactive substance. The detectable tag preferably may be a gold sol particle, the solid support preferably may comprise a microporous membrane, and the first immunoreactive substance may preferably be coupled to the membrane prior to the contacting step. In the preferred form of the invention, during the contacting step, the blocking component, the ambifunctional linking component and the solid phase component are brought into contact with the aqueous sample to produce a test intermediate phase, and the test intermediate phase may thereafter be contacted with the labelled component to produce a test result phase. In this preferred aspect of the invention, the test intermediate phase may be collected before the same is brought into contact with the labelled component, and after such contact has been made to thereby produce the test result phase, the latter may be directly visually inspected for coloration evidencing the presence of gold sol particles therein. In this preferred form of the invention, the test intermediate phase may be collected on a membrane and the test result phase may be visually inspected on the same membrane.

In accordance with the invention, the detectable tag may be a gold sol particle, a component of an enzyme color forming system, or any other sort of detectable tag which is utilizable in connection with immunoassays.

The invention also provides an assay kit for conducting the assay procedures of the invention. The kit may comprise the capture component, the blocking component, the labelled component and the ambifunctional component. In accordance with the more specific aspects of the invention, the assay kit may also include a microporous membrane or filter for collecting and visually inspecting the test result phase.

In another important aspect of the invention, the same provides a hybrid immunoreactive substance comprising at least one antigenic moiety and a proteinaceous antibody moiety, said antigenic moiety and antibody moiety being irreversibly bound together to present the hybrid immunoreactive substance.

DETAILED DESCRIPTION OF THE SPECIFIC ASPECTS OF THE INVENTION

Figure 1:
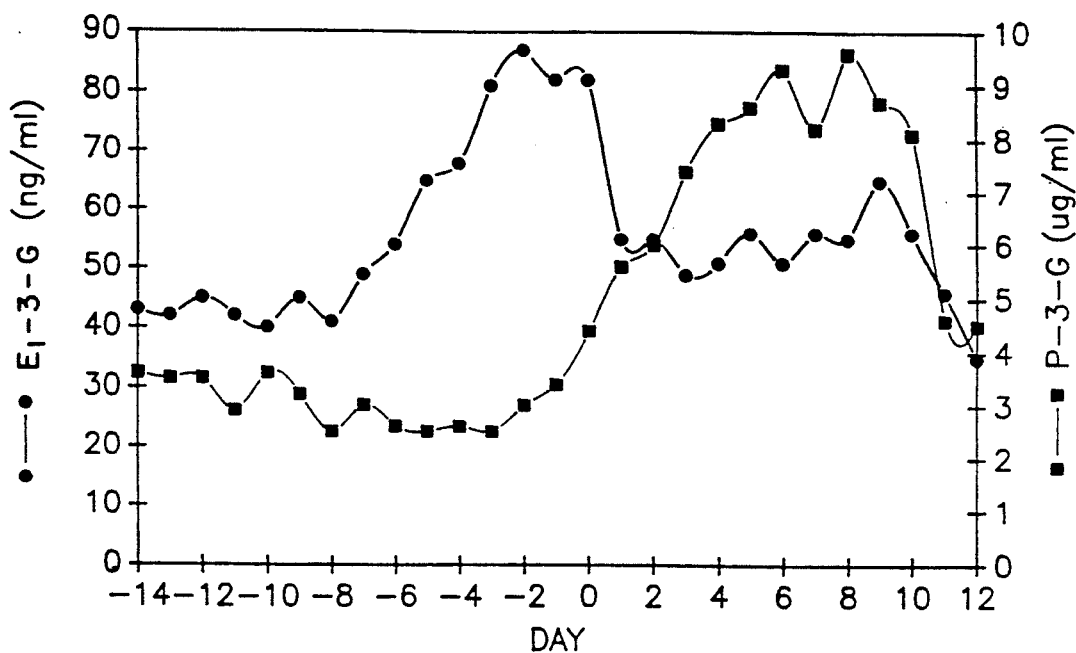
FIG. 1 is a graph illustrating the rhythmic fluctuation of the concentrations of $E_1$-3-G and P-3-G in human urine during the human female menstrual cycle (data are average values from 50 cycles)

The present invention provides an assay procedure for determining the relative concentrations of first and second immunoreactive analytes in an aqueous sample, a kit containing materials for conducting the assay procedure of the invention, and a novel hybrid immunoreactive substance comprising at least one antigenic moiety and a proteinaceous antibody or hormone receptor moiety, which moieties are irreversibly bound together to present an ambifunctional linking compound. As used in the present disclosure, the term ambifunctional is meant to define a molecule which possesses at least one antigenic binding site of an antibody or other receptor and at least one antigenic determinant region of an antigen whereby the ambifunctional molecule is capable of reacting both as an antibody (or receptor) and as an antigen. In the sense of the present invention, the ambifunctional component generally will possess an antigenic binding site of an antibody to or hormone receptor of one of the test analytes and an antigenic determinant region derived from the other of the test analytes. Further details of the ambifunctional component are set forth below.

In its broadest aspects, the invention generally has applicability to any situation where it is desirable to test for the relative concentrations of two different analytes in a single aqueous sample. In particular, the procedure of the present invention has general applicability to situations which call for the determination of the ratio of the concentration of one analyte in an aqueous solution to the concentration of another analyte in an aqueous solution. Thus, the invention presents an assay that is able to measure two analytes simultaneously. In the preferred form of the invention, as set forth hereinbelow, the invention provides a simultaneous dual analyte assay for determining the ratio of estrone-3-glucuronide ($E_1$-3-G) to pregnanediol-3glucuronide (P-3-G) in human urine. Advantageously, the measurement of these steroidal metabolites is useful for bracketing the fertile period in menstruating women. The ratio of $E_1$-3-G to P-3-G provides useful information indicating the beginning of the fertile period some 5 to 6 days prior to ovulation, and the end of the fertile period approximately 2 days after ovulation. The assay involves the use of a solid phase to which P-3-G may be covalently attached; a blocking antibody directed against $E_1$-3-G; the same antibody against $E_1$-3-G labelled with gold; and an ambifunctional linking component.

The assay allows one to differentiate between high and low levels of $E_1$-3-G and P-3-G simultaneously. It is only when the level of $E_1$-3-G is high and the level of P-3-G is low that the assay will yield a coloration which indicates a positive result. The ambifunctional linking component provides a link to which the gold labelled antibody is able to bind. The presence of free P-3-G analyte in the urine inhibits the binding of the ambifunctional linking component to the solid phase. The presence of free $E_1$-3-G analyte in the urine inhibits the binding of a blocking antibody directed to $E_1$-3-G, thus allowing the gold labelled antibody to bind to the ambifunctional bridging component. In this regard, the simultaneous dual analyte assay involves two immunoassays which proceed simultaneously. The urine is assayed for P-3-G using a conventional competitive inhibition assay, and at the same time the urine is assayed for the presence of $E_1$-3-G utilizing a positive step immunoassay of essentially the same character as the positive step immunoassay described in the co-pending, co-assigned application of Izak Bahar, Ser. No. 153,081, filed Feb. 8, 1988 (now U.S. Pat. No. 4,952,517), the entirety of the disclosure of which is hereby incorporated by reference. Thus, at high P-3-G concentrations (i.e, higher than some predetermined, pre-calibrated level) no color is obtainable at any level of $E_1$-3-G. When the level of P-3-G is below the predetermined, pre-calibrated level, color indicating a positive result is obtained whenever the level of $E_1$-3-G is above another predetermined, pre-calibrated level.

With reference to FIG. 1, the levels of $E_1$-3-G and P-3-G in human urine during the menstrual cycle are graphically illustrated. Although the curves are depicted as overlapping, it should be recognized that $E_1$-3-G is plotted on a scale which is compressed by a factor of approximately 1 to 9 relative to the scale of the P-3-G plot, and in actual fact, the curves are not superimposed. This chart simply presents the manner in which the levels of the two hormonal metabolites fluctuate rhythmically during the menstrual cycle.

Figure 2:
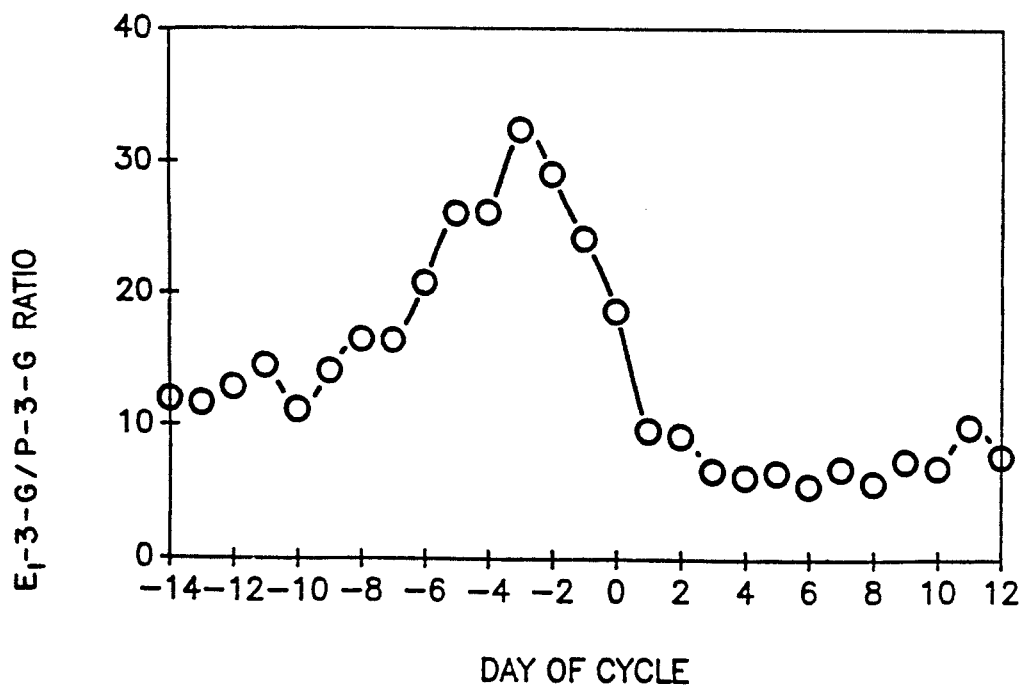
FIG. 2 is a graph illustrating the rhythmic fluctuation of the $E_1$-3-G/P-3-G ratio (data are calculated from FIG. 1 values) during the human female menstrual cycle.

In FIG. 1, day 0 represents the day of ovulation. The fertile period is generally considered to be that period of time extending from approximately 5 to 6 days before ovulation until approximately 2 days after ovulation. The human menstrual cycle may be defined as including a follicular phase (up to ovulation) and a luteal phase (after ovulation). During the follicular phase, estrogens are excreted for regeneration of the endometrium. Ovulation is accompanied by excretion of progestins to instigate the formation of endometriumucosa and thus prepare the uterus for implantation of a fertilized ovum. If implantation does not occur, the level of progestins decreases leading to degeneration of the endometrium and bleeding. The full cycle takes about 28 days. These phenomena may be tracked by following the concentrations of the hormonal metabolites in the urine. Thus, it can be seen from FIG. 1 that during the follicular phase the level of the progestin metabolite P-3-G is relatively low and begins to increase at about the time of ovulation to reach a peak approximately 6 to 8 days after ovulation followed by a subsequent decline back to early follicular phase levels. The level of $E_1$-3-G in the urine is relatively low during the early follicular phase and begins to rise approximately 6 days prior to ovulation and reaches its peak about 2 days before ovulation. The $E_1$-3-G level then falls sharply upon ovulation to resume a relatively low level through the luteal phase and again during the early follicular phase. The ratio of the concentration of $E_1$-3-G to the concentration of P-3-G is plotted in FIG. 2, where it can be seen that the ratio is low during the early follicular phase, and about 6 days before ovulation the ratio begins to raise rapidly so as to reach a peak just before ovulation. The ratio of $E_1$-3-G to P-3-G then falls rapidly upon ovulation to once again resume a low level during the luteal phase of the menstrual cycle. The present invention provides a positive result when the ratio of $E_1$-3-G to P-3-G is high, whereby to bracket the most fertile period of the cycle.

Figure 3:
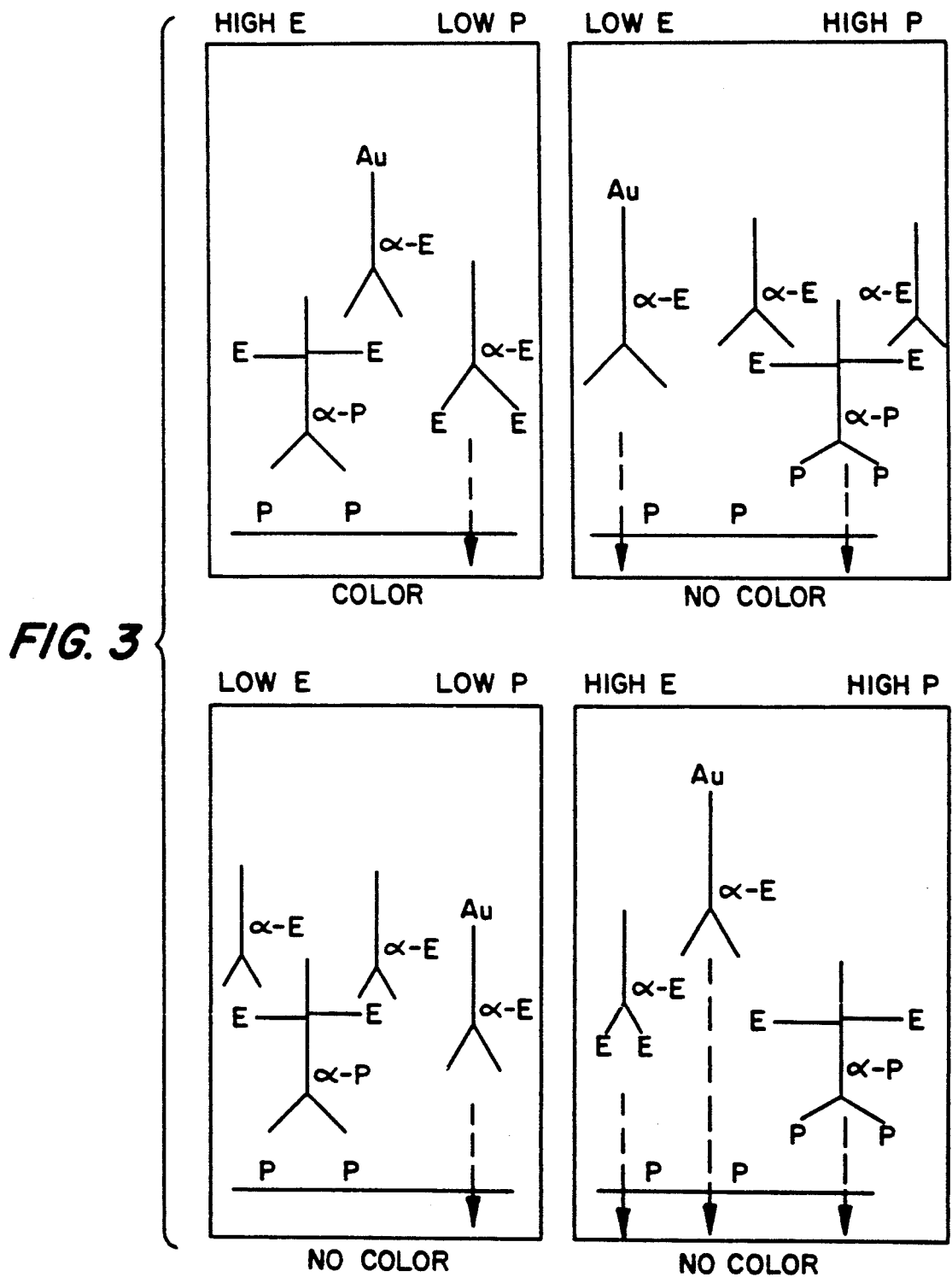
FIG. 3 is a chart schematically illustrating the different conditions which may produce positive or negative results in accordance with the invention.

With regard to FIG. 3, the diagrams schematically illustrate the immunoassay during various phases of the menstrual cycle. In this Figure, the following symbols are used to illustrate the various components:

$E = E_1$-3-G $P = $ P-3-G $|\alpha - E = $ anti $E_1$-3-G antibody $|\alpha - P = $ anti P-3-G antibody — = solid microporous membrane support P P P = solid support with P-3-G bound thereto $\overset{Au}{|}\alpha - E = $ gold labelled anti $E_1$-3-G antibody The upper left hand diagram of FIG. 3 schematically illustrates the immunoassay during the fertile period, that is, when the level of $E_1$-3-G is high and the level of P-3-G is relatively low. In this situation insufficient P-3-G is present in the sample to prevent or inhibit attachment of the ambifunctional linking hybrid component to the solid phase P-3-G. At the same time, the level of $E_1$-3-G in the sample is sufficiently high to tie up the blocking anti $E_1$-3-G antibody and prevent it from blocking the $E_1$-3-G antigenic determinant sites on the ambifunctional linking component. Thus, the $E_1$-3-G antigenic determinant sites of the ambifunctional component are free for binding the gold labelled anti $E_1$-3-G antibody. The gold label is thus bound through the ambifunctional linking component to the solid phase where it can be seen with the naked eye. As illustrated, the solid phase initially consists of a microporous membrane to which P-3-G has been bound, and during the assay unbound components simply proceed through the pores of the membrane as indicated by the arrows and thus are not present on the solid phase capture component during the evaluation of the test results.

The diagram in the upper right hand of the drawing illustrates the luteal phase condition when the concentration of $E_1$-3-G in the sample is low and the concentration of P-3-G in the sample is relatively high. In this situation, the high P-3-G levels in the sample inhibit binding of the ambifunctional linking component to the solid phase P-3-G and all components simply flow through the pores of the membrane and no gold label becomes bound. The lower left hand diagram illustrates the early follicular phase condition where the concentration of each analyte is low. In this case, the ambifunctional linking component binds to the solid phase P-3-G; however, the $E_1$-3-G level is too low to prevent blocking of the $E_1$-3-G determinant sites of the ambifunctional component by the blocking antibody. Thus, the gold labelled antibody does not bind to the solid phase and simply passes through the porous membrane. The diagram in the lower right hand corner illustrates a hypothetical condition where the level of each analyte is relatively high. This probably does not occur during the human menstrual cycle; however, this condition might occur in another system. In this case, the high level of P-3-G in the urine inhibits and prevents binding of the ambifunctional linking component to the solid phase, and thus none of the components of the assay are captured by the solid phase.

In the present disclosure, the following definitions apply.

Definitions

Immunoreactive substance—a substance which is capable of binding specifically with another immunoreactive substance. In the sense of the present disclosure, this terminology is applicable to ligands and receptors including materials which are antigenic, haptenic or possessing antibody type characteristics and including substances which comprise antigenic determinant regions and/or antigen binding sites of antibodies or other receptors.

Analyte—the compound or composition to be detected or determined and which may be a ligand or a receptor.

Immunospecific reactivity—the capability of binding specifically with a binding partner as a result of corresponding antigen binding sites and antigenic determinant regions.

Analogous immunospecific reactivity—the ability to compete immunospecifically with the analogous substance for immunogenic binding sites of an immunospecific binding partner.

Coupled—associated due to covalent or non-covalent binding or some other physical characteristic which causes components which are coupled together to remain together throughout the conduct of the immunoassay.

Adapted to be coupled—possessing a characteristic, such as a reactive group, which permits the substance to become coupled to another substance or object when brought into the proximity thereof. In the sense of the present invention, a component which carries a biotin moiety is "adapted to be coupled" to a solid support or other component which carries an avidin moiety.

Solid support—a solid material which has defined physical size and characteristics that cause it to remain immobile during an immunoassay process, or if mobile, to be susceptible to capture by filtration, sedimentation and/or centrifugation or the like. In the sense of the present invention, the terminology includes microporous membranes, the interior surfaces of test tubes or Microelisa plates, filter elements and solid particles or beads and the like.

Label or detectable tag—a substance coupled to an immunoreactive substance which facilitates detection of the immunoreactive substance at an advantageous point in time. Presently known labels or tags include gold sol particles, participants in enzymatic color forming reactions, fluorescent materials, radioactive materials, and the like.

Ambifunctional—a characteristic which is the result of the simultaneous possession of both at least one antigenic determinant region and at least one antigen binding site. Such antigen binding sites are capable of immunochemically binding corresponding antigenic determinant regions of antigens and are functional components of antibodies and other receptors. A substance is ambifunctional in the sense of the present disclosure when it is able to react immunospecifically both as a ligand and as a receptor.

Hybrid—in the sense of the present disclosure, the term hybrid simply refers to a compound or composition which includes immunospecifically reactive sites from two or more ligands and/or receptors and which sites have been irreversibly bound or coupled together by some extraneous means.

Immunoreactive site—a site on a substance or compound which is capable of reacting immunospecifically with a binding-partner, for example, an antibody variable region or an antigenic determinant region.

The invention is further illustrated by way of the following Examples:

EXAMPLE I

Preparation of Ambifunctional Hybrid Linking Component

An ambifunctional hybrid linking conjugate containing at least one antigen binding site of an anti P-3-G antibody molecule and a plurality of antigenic determinant regions of an $E_1$-3-G molecule was prepared using the carbodiimide method of Goodfriend et al. described in an article entitled "Antibodies to Bradykinin and Angiotensin: A Use of Carbodiimides in Immunology", *Science (Washington)*, Vol. 144, pp 1344–6 (12 June 1964). Thus, a solution containing anti P-3-G antibodies was concentrated and dialyzed against 0.15 M NaCl at 4° C. The resultant solution had an antibody concentration of 11.5 mg/ml, and a 1.5 ml portion thereof thus contained 17.25 mg of ($1.078 \times 10^{-4}$ moles) of the anti p-3-G antibody. 22 mg ($4.4 \times 10^{-4}$ mmoles) of $E_1$-3-G were dissolved in 0.5 ml of $H_2O$ and 1.5 ml of the anti P-3-G antibody solution were added to produce a mixture containing an approximate 1:400 mol/mol ratio of anti P-3-G antibody (MW=160,000) to $E_1$-3-G (MW=500) 16 mg of the water soluble carbodiimide, 1-ethyl-3-(3-dimethylaminopropyl) carbodiimide HCl (Sigma) (MW=191.7), were dissolved in the mixture containing the anti P-3-G antibody and the $E_1$-3-G, and the resultant admixture was allowed to react at room temperature for one hour. The reaction product was diluted on a 1:2 basis in PBS/Azide, was dialyzed against PBS/Azide (pH 7.4) and was filtered through a 0.22 micron filter (Gelman). The final volume was 4 ml.

EXAMPLE II

Dual Analyte Assay

Materials

Standards

Pregnanediol-3α-Glucuronide (P-3-G) (Sigma) was dissolved in a 50% solution of ethanol in water. Concentrations of 0.156 µg/ml and 0.625 µg/ml were made up in a 0.1% solution of gelatin in PBS (pH 7.4) and 0.02 NaAzide.

Estrone-β-D-glucuronide ($E_1$-3-G) standards were prepared in essentially the same manner to provide concentrations of 0, 0.156, 0.3125, 0.625, 1.25 and 5 µg/ml.

Blocking Antibody

Anti $E_1$-3-G antibody was diluted in 2.5% PEG 8000 in PBS (pH 7.4) and 0.02% NaAzide to provide a concentration of 512 µg/l.

Ambifunctional Hybrid Linking Component

The conjugate prepared in accordance with Example I and comprising an ambifunctional hybrid molecule containing at least one antigen binding site of an anti P-3-G antibody and a plurality of $E_1$-3-G antigenic determinant regions was diluted at a dilution ratio of 1:40 in a 1% solution of BSA in PBS (pH 7.4) containing 0.02% NaAzide.

Labelled Component

Anti $E_1$-3-G antibody was labelled with gold sol particles prepared using the Frens procedure essentially as described in Example I of co-pending application Ser. No. 105,285 (now U.S. Pat. No. 4,859,612), the entirety of the disclosure of which application is hereby specifically incorporated by reference. In this regard, 12.32 ml of a 100 mM sodium borate buffer solution (pH =10.5) was rapidly admixed with 164.25 ml of the gold sol dispersion containing particles having an average diameter of approximately 60–90 nM. While mixing, 36.5 ml of a 188 µg/ml solution of the antibody in 2 mM borate buffer were added and allowed to react for 15 minutes. 16.4 ml of 5% polyethylene glycol (PEG) 20 M (Sigma, St. Louis) were added while mixing, and the admixture was allowed to react for 15 minutes of room temperature. The gold labelled antibody solution was placed in a Sorvall GSA rotor and centrifuged three times at 10,000 rpm in a Sorvall RC5B centrifuge. After each centrifugation the supernatent was discarded and the red pellet was resuspended in Johnson's Buffer (0.6 g/L Trizma Base, 0.01 g/L PEG (20 M) and 0.01 g/L Thimerosal in purified water, plus sufficient HCl, if necessary, to adjust the pH to 9.0). The solution was filtered through a 0.22 micron filter and brought up to a volume of 46.9 ml using Johnson's Buffer. Finally, the antibody solution was diluted at a dilution ratio of 1:20 in a solution containing 40 mM $MgSO_4$, 1% BSA and 0.02% NaAzide.

Solid Phase Component

Gelatin/P-3-G was prepared by direct coupling using a water soluble carbodiimide. In this procedure, 150 mg of gelatin were dissolved in 4 ml of warm water and 1 ml of pyridine was added to produce 5 ml of solution containing 20% pyridine in water. In a separate container, 20 mg of P-3-G were dissolved in 0.2 ml of pyridine and sufficient water was added to produce one ml of solution containing 20% pyridine. 1 ml of the gelatin solution was mixed with 0.625 ml of the P-3-G solution and 9.55 mg of 1-ethyl-3-(3 dimethylaminopropyl) carbodiimide HCl were added and dissolved. The mixture was allowed to react with mixing for two hours at room temperature. The solution was dialyzed against warm PBS/Azide and diluted with PBS/Azide to a final gelatin concentration of approximately 1 mg/ml. The gelatin P-3-G solution was then spotted onto and the gelatin P-3-G immobilized on a number of Millipore Immobilon activated microporous membranes (0.65 micron) using 10 ml of the 1 mg/ml solution for each. After spotting, the membranes were blocked by immersion for 5 minutes in a straight monoethanolamine solution.

Washing Solution 0.2% Igepal in $H_2O$.

Assay Procedure

1. Samples were made up to include all combinations of the various standard hormone concentrations outlined above.

2. Twelve tubes were provided and to each tube, 80 µl of sample, 25 µl of anti $E_1$-3-G antibody (blocking antibody) solution (512 µg/l), and 20 µl of the diluted solution of the ambifunctional hybrid linking component were added sequentially with mixing between each addition.

3. The mixtures from step 2 were each poured through a solid phase, gelatin/P-3-G spotted membrane mounted in a flow through assay (FTA) device essentially of the type disclosed in co-pending, coassigned application Ser. No. 107,240, filed Oct. 29, 1987 (now U.S. Pat. No. 4,999,163).

4. 0.2 ml of the diluted solution of the gold labelled component was then poured through the membrane.

5. The membrane was washed by pouring the washing solution through the membrane until the cup of the FTA device was full.

6. The results were determined by visual inspection and observation of the membranes for development of the pink color that is characteristic of the presence of gold particles. The results are tabulated in Table I where it can be seen that the samples containing high concentrations of P-3-G (0.625 µg/ml) produced no coloration on the membrane no matter what the concentration of $E_1$-3-G. At low concentrations of P-3-G (0.156 µg/ml) the samples containing low concentrations of $E_1$-3-G (0.3125 µg/ml and below) produced no coloration while the samples containing high concentrations of $E_1$-3-G (above 0.3125 µg/ml) resulted in the production of a vivid pink coloration.

TABLE I

| Concentration of $E_1$-3-G (µg/ml) Concentration of P-3-G (µg/ml) | 0 | 0.156 | 0.3125 | 0.625 | 1.25 | 5 |
|---|---|---|---|---|---|---|
| 0.156 | — | — | — | — | — | — |
| 0.625 | — | — | — | + | + | + |

In the above Table, the minus sign (—) indicates no color formation and the plus sign (+) indicates vivid color formation.

In the foregoing Example, the solid support consisted of a microporous membrane. The solid component was prepared by coupling P-3-G to the microporous membrane using a gelatin linkage. Thus, in this case, the first immunospecific substance, which is P-3-G itself, was initially coupled to the solid support prior to the contacting step (step 3 in the Example II assay procedure).

As a result of the contacting step, the ambifunctional hybrid linking component bound to the P-3-G on the solid support in those instances where the amount of P-3-G analyte in the sample was insufficient to inhibit binding. In instances where the concentration of P-3-G was greater than a pre-calibrated amount, the ambifunctional hybrid component simply passed through the membrane. In any event, whatever is present on the membrane after the contacting step may be broadly characterized as a test intermediate phase. In the case of low P-3-G, the intermediate phase included ambifunctional hybrid linking component bound to the P-3-G on the solid component, and in the event of high P-3-G in the sample, the intermediate phase included only the solid phase component comprising unreacted P-3-G attached to the membrane. Where the $E_1$-3-G was sufficiently high in the original sample, the $E_1$-3-G antigenic determinant regions of the ambifunctional hybrid linking component of the test intermediate phase remained unblocked, whereas in those instances where the $E_1$-3-G level in the sample solution was below the preselected level, the $E_1$-3-G antigenic determinant sites on the ambifunctional hybrid component became blocked by the blocking anti $E_1$-3-G antibody. In any event, the various test intermediate phases were contacted with the gold labelled component in step 4, and in those instances where the ambifunctional hybrid linking component was bound to the solid component and the $E_1$-3-G antigenic determinant regions thereof remained unblocked, the labelled component bound to the ambifunctional component and thus became bound to the solid support. In all other instances the labelled component simply flowed through the membrane. Thus, a pink test result phase was produced in those instances where the concentration of $E_1$-3-G was high and the concentration of P-3-G was low in the test sample and in all other instances the test result phase remained uncolored.

EXAMPLE III

Dual Analyte Assay

Materials

Standards

P-3-G and $E_1$-3-G samples were dissolved in 50% ethanol in water and P-3-G concentrations of 1.25, 2.5 and 5 µg/ml and $E_1$-3-G concentrations of 0.625, 0.3125, 0.156, 0.078 and 0.039 µg/ml were made up in a 0.1% solution of BSA in PBS (pH 7.4).

Blocking Antibody

Same as in Example II except the concentration of the anti $E_1$-3-G antibody in the solution was 128 µg/ml.

Ambifunctional Hybrid Component

Same as in Example II except the Example I conjugate was diluted at a dilution ratio of 1:150.

Labelled Component

Anti $E_1$-3-G antibody was labelled with gold sol particles prepared using the Frens procedure. In this case, 12.79 ml of a 100 mM sodium borate buffer solution (pH=10) were rapidly admixed with 170.5 ml of the gold sol dispersion containing particles having an average diameter of approximately 56 nM. While mixing, 37.8 ml of a 180 µg/ml solution of the in 2 mM borate buffer were added and allowed to react for 15 minutes. 17.5 ml of 5% polyethylene glycol (PEG) 20 M (Sigma, St. Louis) were added while mixing and the admixture was allowed to react for 15 minutes of room temperature. The gold labelled antibody solution was placed in a Sorvall GSA rotor and centrifuged three times at 10,000 rpm in a Sorvall RC5B centrifuge. After each centrifugation the supernatent was discarded and the red pellet was resuspended in Johnson's Buffer (pH 9.0). Finally, the solution was filtered through a 0.22 micron filter and brought up to a volume 5.2 ml using Johnson's Buffer. The antibody solution was diluted at a dilution ratio of 1:100 in a solution containing 40 mM $MgSO_4$, 1% BSA and 0.02% NaAzide.

Solid Phase Component

In this Example, the solid phase component consisted of a biotinylated gelatin/P-3-G G (BGP) component which facilitated capture of the composite on an avidin spotted membrane.

A. Biotinylated Gelatin/P-3-G (BGP)—Gelatin/P-3-G was prepared by dissolving 8.27 mg P-3-G in a 20% solution of pyridine in water to a total volume of 0.276 ml (30 mg P-3-G/ml). 20 mg of gelatin were also dissolved in a 20% solution of pyridine in water to a total volume of 0.485 ml (41.2 mg gelatin/ml). The solutions of P-3-G and gelatin were mixed together to produce an admixture containing a P-3-G to gelatin mole ratio of 50 to 1, and 8 mgs of the water soluble carboniimide used in Examples I and II were added and the mixture allowed to react of room temperature for 1 hour. The reaction product was dialyzed against PBS/Azide and the concentration adjusted so that the final solution contained 13.0 mg gelatin/ml. The solution was further diluted to a gelatin concentration of 1 mg/ml using 0.1 M sodium bicarbonate (pH=8.0) and 0.585 ml of a 1 mg/ml solution of biotin-LCNHS in DMSO was added to 3.9 ml of the diluted gelatin/P-3-G solution. The mixture was allowed to react for 4 hours at room temperature. The biotinylated gelatin/P-3-G (BGP) produced was then dialyzed against PBS/Azide and the BGP solution diluted at a ratio of 1:32 in PBS.

B. Avidin Spotted Membrane—20 µl of a 2.5 mg/ml solution of avidin in PBS and containing 10 mg/ml of 4 dimethylamino pyridine was spotted onto and the avidin immobilized on each of a number of Millipore Immobilon microporous activated membranes (0.65 micron). The avidin spotted membranes were then blocked with 10% ethanolamine in carbonate buffer (1 M—pH 9.5) overnight.

Assay Procedure

1. Samples were made up to include all combinations of the various standard hormone concentrations outlined above.

2. Fifteen tubes were provided, and to each tube, 50 µl of sample, 25 µl of anti $E_1$-3-G antibody solution diluted BGP solution and 20 (128 µg/l), 20 µl of the µl of the diluted ambifunctional hybrid linking component were added sequentially with mixing between each addition.

3. The mixtures from step 2 were each poured through a solid phase avidin spotted membrane mounted in a flow-through assay (FTA) device of the same sort as was used in Example II.

4. 0.2 ml of the diluted solution of the gold labelled component was then poured through each membrane.

5. Each membrane was washed by pouring the washing solution through the membrane until the cup of the FTA device was full.

6. The results were determined by visual inspection and observation of the membranes for development of the pink color that is characteristic of the presence of gold particles. The results are tabulated in Table II where it can be seen that the samples containing low concentrations of $E_1$-3-G produced little or no coloration on the membrane no matter what the concentration of P-3-G. At high $E_1$-3-G levels the production of color varied inversely with the P-3-G concentration. That is to say, samples containing high concentrations of $E_1$-3-G and high concentrations of P-3-G resulted in the production of less coloration than samples containing high concentrations of $E_1$-3-G and low concentrations of P-3-G.

TABLE II

| Concentration of $E_1$-3-G (µg/ml) Concentration of P-3-G (µg/ml) | 0.39 | 0.78 | 0.156 | 0.3125 | 0.625 |
| --- | --- | --- | --- | --- | --- |
| 1.25 | 0 | 0 | ½ | 4 | 4 |
| 2.5 | 0 | 0 | 0 | 2 | 2 |
| 5 | 0 | 0 | 0 | 1 | 1 |

In the above Table, 0 indicates no visible color formation, and the higher the number, the more intense was the color formation.

In Example III, the solid phase component comprised an immunoreactive substance, that is P-3-G, which was adapted to be coupled to a solid support. In this Example, gelatin/P-3-G was biotinylated and coupled to an avidin spotted support (the microporous membrane) after the contacting step. Thus, in step 2, the sample, the blocking antibody, the BGP solution and the ambifunctional hybrid component were all mixed together prior to being brought into contact in step 3 with the avidin spotted membrane. In those instances where the concentration of $E_1$-3-G was high and the concentration of P-3-G was low in the sample, an immunocomposite was formed in step 2 that comprised the labelled component, the ambifunctional hybrid component and the solid phase component. Such immunocomposite was collected as an intermediate test phase by reaction between the biotin and the avidin when the mixture was contacted with the avidin spotted membrane in step 3. The test intermediate phase was then contacted with the gold label component in step 4, all as is set forth in connection with Example II above, to produce a test result phase which was pink when $E_1$-3-G was high and P-3-G was low in the sample and which was otherwise uncolored or only faintly colored.

In the above descriptions, the capture component consisted of an immunoreactive substance (P-3-G) which was either coupled to or was adapted to be coupled to a solid phase microporous, flow through type membrane. Alternatively, the capture reaction component might be composed of an immunoreactive substance coupled to a dispersible, water insoluble, solid phase particle, similar to the solid phase component fully disclosed in U.S. Pat. No. 4,859,612. In such event, the capture reaction component would comprise a first immunoreactive substance (P-3-G) which is initially coupled to a latex particle, Sepharose bead, glass bead, etc., and an immunocomposite comprising the capture component, the labelled component and the ambifunctional component would be produced in the event of a positive result. Such immunocomposite could then be collected, in the manner described in said Cole application, utilizing a porous matrix capture element, sedimentation and/or centrifugation to present a test result phase collected on the porous matrix capture element for visual inspection.

The present invention involves the use of the positive step assay of Bahar as set forth in U.S. Pat. No. 4,952,517, as well as FTA devices of the sort disclosed in U.S. Pat. No. 4,999,163 and, at least in certain aspects, the metal sol capture immunoassay procedures of Cole et al. as set forth in U.S. Pat. No. 4,859,612. Accordingly, the entireties of the disclosures of said '517, '163 and '612 Patent are specifically incorporated herein by reference.

The present invention provides the immunoassay procedures outlined above. The invention also provides kits of materials containing measured quantities of the test components to facilitate conduct of a single or a multiplicity of replicated tests. The invention also provides a novel ambifunctional reaction component which comprises at least one antigenic moiety and a proteinaceous receptor moiety, which moieties are irreversibly bound together to present the ambifunctional component. Such an ambifunctional hybrid component and a method for producing the same are set forth above in Example I.

In accordance with the invention, and is well known to those of ordinary skill in the art to which the present invention pertains, immunoassays generally must be calibrated for detection and/or determination of specifically sought after results. The concentrations and/or constructions of the various components of the assay must be calibrated, usually empirically, using standards or the like, to provide the desired sensitivity and/or calibration. Thus, the amount of the immunoreactive substance of the capture reaction component is adjustable simply by coupling more or less of the substance to the solid support. The capture component substance competes with one of the analytes for binding sites on the ambifunctional component, and thus the amount of the capture component immunoreactive substance may be adjusted to calibrate the level of analyte which will cause a positive result. Likewise, the amount of blocking reaction component may be adjusted to adjust the level of the second immunoreactive analyte which provides a positive test.

The amount of the ambifunctional reaction component and the ratio of first immunoreactive sites to second immunoreactive sites thereon may also be adjusted to further calibrate and/or sensitize the assay. These manipulations are all within the routine skill of one of ordinary skill in the art to which the present invention pertains, and are the type of manipulations which generally are necessary in constructing immunoassay procedures. Suffice it to say that the ambifunctional reaction component of the present invention is novel, and because of its novel construction the flexibility of the fine tuning of the assay is maximized.

We claim:

1. An assay procedure for determining the relative concentrations of first and second immunoreactive analytes in an aqueous sample, said assay procedure comprising:

providing a capture reaction component comprising a first immunoreactive substance which binds the same specific winding partner as said first immunoreactive analyte, said first immunoreactive substance initially being coupled to a solid support providing a blocking reaction component comprising a second immunoreactive substance which binds immunospecifically with said second immunoreactive analyte;

providing a labelled reaction component comprising a third immunoreactive substance and a detectable tag coupled thereto, said third immunoreactive substance winding the same specific binding partner as said second immunoreactive substance;

providing an ambifunctional reaction component comprising a hybrid immunoreactive substance having at least a first immunoreactive site which binds immunospecifically with said first immunoreactive analyte and with said first immunoreactive substance and at least a second immunoreactive site which binds the same specific binding partner as said second immunoreactive analyte, said second site thus binding immunospecifically with said second and third immunoreactive substances;

contacting the aqueous sample with (1) said capture reaction component, (2) an amount of said ambifunctional component that is sufficiently low relative to the capture reaction component that binding between the first immunoreactive site of the hybrid substance and the first immunoreactive substance of the capture component is inhibited by the presence of at least a predetermined concentration of said first analyte in the sample to such a degree that the amount of ambifunctional component able to bind to the first immunoreactive substance is too low to support a positive assay result, (3) said labelled reaction component, and (4) an amount of said blocking component that is sufficiently large to block the second immunoreactive sites of the hybrid substance and inhibit binding between the latter and the second immunoreactive substance of said labelled component in the absence of at least a preselected concentration of said second analyte in the sample to such a degree that the amount of labelled component able to bind to the second site of said hybrid substance is too low to support a positive assay result, whereby a positive assay result is achievable only when the concentration of first analyte in the sample is less than said predetermined concentration and the concentration of second analyte in the sample is more than said preselected concentration to thereby produce a determinable quantity of an immunocomposite that comprises both the capture component and the labelled reaction component.

2. An assay procedure as set forth in claim 1, wherein at least one of said immunoreactive analytes is antigenic.

3. An assay procedure as set forth in claim 2, wherein said first and second immunoreactive analytes are each antigenic.

4. An assay procedure as set forth in claim 3, wherein said first and second immunoreactive analytes are each steroidal.

5. An assay procedure as set forth in claim 4, wherein said first and second immunoreactive analytes are each hormonal.

6. An assay procedure as set forth in claim 5, wherein said first and second immunoreactive analytes are each naturally occurring mammalian steroid hormones or metabolites thereof.

7. An assay procedure as set forth in claim 6, wherein said first immunoreactive analyte is P-3-G and said second immunoreactive analyte is $E_1$-3-G.

8. An assay procedure as set forth in claim 1, wherein the solid support comprises a microporous membrane.

9. An assay procedure as set forth in claim 1, wherein the solid support comprises a dispersible, water insoluble particle, said first immunoreactive substance being coupled to the particle prior to the contacting step.

10. An assay procedure as set forth in claim 9, wherein said detectable tag is a gold sol particle.

11. An assay procedure as set forth in claim 10, wherein during the contacting step, the blocking component, the ambifunctional component and the labelled component are brought into contact with the sample to produce an immunocomposite containing the water insoluble particle and the gold sol particles when the test is positive.

12. An assay procedure as set forth in claim 11, wherein is included the step of collecting the immunocomposite and directly visually inspecting the same for coloration evidencing the presence of gold in the collected mass.

13. An assay procedure as set forth in claim 12, wherein the immunocomposite is collected and visually inspecting on a filter element.

14. An assay procedure as set forth in claim 1, wherein said hybrid immunoreactive substance includes a first proteinaceous substance comprising said first immunoreactive site and a second proteinaceous substance comprising said second immunoreactive site, said first and second proteinaceous substances being irreversibly bound together to present said hybrid substance.

15. An assay procedure as set forth in claim 1, wherein during said contacting step said sample is contacted with the blocking component before it is contacted with the labelled component.

16. An assay procedure as set forth in claim 1, wherein during said contacting step, the blocking component, the ambifunctional component and the solid phase component are brought into contact with the aqueous sample to produce a test intermediate phase and the test intermediate phase is contacted with the labelled component to produce a test result phase.

17. An assay procedure as set forth in claim 16, wherein the first immunoreactive substance is coupled to the solid support prior to the contacting step.

18. An assay procedure as set forth in claim 16, wherein the first immunoreactive substance is coupled to the solid support after the contacting step.

19. An assay procedure as set forth in claim 1 for predicting the fertile period of the menstrual cycle and wherein said first analyte is P-3-G, said second analyte is $E_1$-3-G, said first immunoreactive substance is P-3-G, said second and third immunoreactive substances are the same antibody to $E_1$-3-G, said first immunoreactive site is provided by an antigen binding site of an antibody to P-3-G and said second immunoreactive site is provided by an antigenic determinant region of an $E_1$-3-G molecule.

20. An assay procedure as set forth in claim 19, wherein said antibody to P-3-G and said $E_1$-3-G molecule are irreversibly bound together to present said hybrid immunoreactive substance.

21. An assay procedure as set forth in claim 20, wherein said detectable tag is a gold sol particle.

22. An assay procedure as set forth in claim 21, wherein said solid support comprises a microporous membrane and said first immunoreactive substance is coupled thereto prior to the contacting step.

23. An assay procedure as set forth in claim 22, wherein during said contacting step, the blocking component, the ambifunctional component and the solid phase component are brought into contact with the aqueous sample to produce a test intermediate phase and the test intermediate phase is thereafter contacted with the labelled component to produce said test result phase.

24. An assay procedure as set forth in claim 23, wherein is included the step of collecting the test intermediate phase before the same is brought into contact with the labelled component, and directly visually inspecting the test result phase for coloration evidencing the presence of gold sol particles therein.

25. An assay procedure as set forth in claim 24, wherein the test intermediate phase is collected on the membrane and the test result phase is visually inspected on said membrane.

26. An assay procedure as set forth in claim 1, wherein said detectable tag is a gold sol particle.

27. An assay procedure as set forth in claim 1, wherein said detectable tag is a component of an enzyme color forming system.

28. An assay procedure as set forth in claim 1, wherein during said contacting step said aqueous sample is contacted with the capture component before it is contacted with the labelled component.

29. An assay procedure as set forth in claim 1, wherein said first immunoreactive substance of the capture component is initially coupled to a solid support prior to the contacting step.

30. An assay procedure as set forth in claim 1, wherein said first immunoreactive substance of the capture component is coupled to a solid support during or after the contacting step.

31. An assay procedure as set forth in claim 28, wherein the first immunoreactive substance of the capture component is coupled to a solid support after the aqueous sample is contacted with the capture component and before the aqueous sample is contacted with the labelled component.

32. An assay procedure as set forth in claim 28, wherein the first immunoreactive substance of the capture component is coupled to a solid support after the aqueous sample is contacted with the capture component and before the aqueous sample is contacted with the labelled component.

33. An assay kit for conducting the assay procedure of claim 1, said kit comprising said capture component, said blocking component, said labelled component and said ambifunctional component being an antibody variable region which binds said antigenic determinant region of said first immunoreactive analyte and said second immunoreactive site on said ambifunctional component being an antigenic determinant region that is the same as said antigenic determinant region of said second immunoreactive analyte.

34. An assay kit for conducting the assay procedure of claim 8, said kit comprising said capture component, said blocking component, said labelled component, said ambifunctional component and said microporous membrane, said analytes each having an antigenic determinant region, said first immunoreactive site on said ambifunctional component being an antibody variable region which binds said antigenic determinant region of said first immunoreactive analyte and said second immunoreactive site on said ambifunctional component being an antigenic determinant region that is the same as said antigenic determinant region of said second immunoreactive analyte.

35. An assay kit for conducting the assay procedure of claim 21, said kit comprising said capture component, said blocking component, said labelled component and said ambifunctional component.

36. An assay kit for conducting the assay procedure of claim 24, said kit comprising said capture component, said blocking component, said labelled component, said ambifunctional component and an element for collecting the test intermediate phase and visually inspecting the test result phase.

37. An assay kit for conducting the assay procedure of claim 25, said kit comprising said capture component, said blocking component, said labelled component, said ambifunctional component and a filter for collecting the test intermediate phase and visually inspecting the test result phase.

38. An assay kit for conducting the assay procedure of claim 1, said kit comprising said capture component, said blocking component, said labelled component and said ambifunctional component, said analytes each having an antibody variable region, said first immunoreactive site on said ambifunctional component being an antigenic determinant region that binds with said antibody variable region of said first immunoreactive analyte and said second immunoreactive site on said ambifunctional component being an antibody variable region that is the same as said antibody variable region of the second immunoreactive analyte.

39. An assay kit for conducting the assay procedure of claim 8, said kit comprising said capture component, said blocking component, said labelled component, said ambifunctional component and said microporous membrane, said analytes each having an antibody variable region, said first immunoreactive site on said ambifunctional component being an antigenic determinant region that binds with said antibody variable region of said first immunoreactive analyte and said second immunoreactive site on said ambifunctional component being an antibody variable region that is the same as said antibody variable region of the second immunoreactive analyte.

40. A hybrid immunoreactive substance for use in simultaneously measuring the concentration of first and second immunoreactive analytes in a single aqueous sample, said substance comprising at least one antigenic moiety and a proteinaceous receptor moiety, said antigenic moiety and the receptor moiety being irreversibly bound together to present said substance and each said moiety being immunospecifically active in making said simultaneous measurement, wherein said moieties do not specifically bind one another, said analytes each having an antigenic determinant region, said antigenic moiety including an antigenic determinant region which is the same as said antigenic determinant region of the first analyte and said receptor moiety including an antibody variable region which binds with the antigenic determinant region of the said analyte, said second analyte being P-3-G.

41. A hybrid immunoreactive substance for use in simultaneously measuring the concentration of first and second immunoreactive analytes in a single aqueous sample, said substance comprising at least one antigenic moiety and a proteinaceous receptor moiety, said antigenic moiety and the receptor moiety being irreversibly bound together to present said substance and each said moiety being immunospecifically reactive in making said simultaneous measurement, wherein said moieties do not specifically bind one another, said analytes each having an antigenic determinant region, said antigenic moiety including an antigenic determinant region which is the same as said antigenic determinant region of the first analyte and said receptor moiety including an antibody variable region which binds with the antigenic determinant region of the said analyte, said first analyte being $E_1$-3-G.

42. A substance as set forth in claim 40, wherein said first analyte is $E_1$-3-G.

* * * * *